United States Patent [19]

Dasch et al.

[11] Patent Number: 5,772,998
[45] Date of Patent: Jun. 30, 1998

[54] MONOCLONAL ANTIBODIES TO TRANSFORMING GROWTH FACTOR-BETA AND METHODS OF USE

[75] Inventors: James R. Dasch, Palo Alto; Doran R. Pace, III, San Francisco; Wendy O. Waegell, Mountain View, all of Calif.

[73] Assignee: Celtrix Pharmaceuticals, Inc., Santa Clara, Calif.

[21] Appl. No.: 434,976

[22] Filed: May 4, 1995

Related U.S. Application Data

[62] Division of Ser. No. 759,109, Sep. 6, 1991, Pat. No. 5,571,714, which is a continuation of Ser. No. 288,432, Dec. 22, 1988, abandoned.

[51] Int. Cl.$^6$ .......................... A61K 39/395; C07K 16/22
[52] U.S. Cl. ..................................... 424/133.1; 424/145.1; 424/158.1; 530/387.3; 530/388.23; 530/388.24; 530/389.2
[58] Field of Search ............................... 424/145.1, 158.1, 424/198.1, 133.1; 435/70.21, 172.2, 240.27; 530/388.23, 388.24, 389.2, 399, 387.3

[56] References Cited

U.S. PATENT DOCUMENTS 4,774,322  9/1988  Seyedin et al. .

FOREIGN PATENT DOCUMENTS

| 0455482 | 11/1991 | European Pat. Off. . |
|---|---|---|
| WO 91/19513 | 12/1991 | WIPO . |
| WO 94/18991 | 9/1994 | WIPO . |

OTHER PUBLICATIONS

Roberts et al., "Type β transforming growth factor: a bifunctional regulator of cellular growth" *Proc. Natl. Acad. Sci. USA* (1985) 82:119–123.
Hayashi et al., "Differential effects of TGF-$\beta_1$ on lymphohemopoiesis in long–term bone marrow cultures" *Blood* (1989) 74(5):1711–1717.
Carlino et al., "Transforming growth factor β1 systematically modulates granuloid, erythroid, lymphoid, and thrombocytic cells in mice" *Exp. Hematol.* (1992) 20:943–950.
Han et al., "Megakaryocytopoiesis: characterization and regulation in normal and pathologic states" *Int. J. Hematol.* (1991) 54(1):3–14.
Ishibashi et al., "Type β transforming growth factor is a potent inhibitor of murine megakaryocytopoiesis in vitro" *Blood* (1987) 69:1737–1741.
Keller et al., "Transforming growth factor β directly regulates primitive murine hematopoietic cell proliferation" *Blood* (1990) 75:596–602.
Cashman et al., "Mechanisms that regulate the cell cycle of very primitive hematopoietic cells in long–term human marrow cultures. I. Stimulatory role of a variety of mesenchymal cell activators and inhibitory role of TGF–β" *Blood* (1990) 75(1):96–101.
Ellingsworth et al., "Antibodies to the N–terminal portion of cartilage–inducing factor A and transforming growth factor β" *J. Biol. Chem.* (1986) 261:12362–12367.

Eaves et al., "Mechanisms that regulate the cell cycle status of very primitive hematopoietic cells in long–term human marrow cultures. II. Analysis of positive and negative regulators produced by stromal cells within the adherent layer" *Blood* (1991) 78(1):110–117.
Hatzfeld et al., "Release of early human hematopoietic progenitors form quiescence by antisense transforming growth factor β1 or Rb oligonucleotides" *J. Exp. Med.* (1991) 174:925–929.
Wang et al., "Expression cloning and characterization of the TGF–β type III receptor" *Cell* (1991) 67:797–805.
Jordan et al., "Cellular and developmental properties of fetal hematopoetic stem cells" *Cell* (1990) 61;953–963.
Waegell et al., "Neutralizing antibody to TGF–β overcomes normal growth controls in long–term bone marrow cultures" *J. Cell. Biochem.* (1992) 16:92 (abstract No. M342).
Dasch et al., "Monoclonal antibodies recognizing transforming growth factor–β. Bioactivity neutralization and transforming growth factor β2 affinity purification" *J. Immunol.* (1989) 142:1536–1547.
Herlyn et al., "Growth–regulatory factors for normal, premalignant, and malignant human cells in vitro" *Adv. Cancer. Res.* (1990) 54:213–234.
Harris et al., "Therapeutic antibodies—the coming of age" *TIBTECH* (1993) 11:42–44.
Lucas et al., "The autocrine production of transforming growth factor–$\beta_1$ during lymphocyte activation" *J. Immunol.* (1990) 145:1415–1422.
Galfrè et al., "Preparation of monoclonal antibodies: strategies and procedures" *Meth. Enzymol.* (1981) 73:3–46.
Cheifetz et al., "The transforming growth factor–β system: A complex pattern of cross–reactive ligands and receptors" *Cell* (1987) 48:409–416.
Ellingsworth et al., "Transforming growth factor–βs are equipotent growth inhibitors of interleukin–1–induced thymocyte proliferation" *Cell. Immunol.* (1988) 114:41–54.
Kehrl et al., "Production of transforming growth factor–β by human T lymphocytes and its potential role in the regulation of T cell growth" *J. Exp. Med.* (1986) 163:1037–1050.
Kehrl et al., "Transforming growth factor β is an important immunomodulatory protein for human B lymphocytes" *J. Immunol.* (1986) 137:3855–3860.
Keller et al., "Transforming growth factor β–1 selectively regulates early murine hematopoietic progenitors and inhibits the growth of IL–3–dependent myeloid leukemia cell lines" *J. Exp. Med.* (1988) 168:737–750.
Keski–Oja et al., "Immunodetection and modulation of cellular growth with antibodies against mative transforming growth factor–$\beta^1$" *Cancer Res.* (1987) 47:6451–6458.

(List continued on next page.)

*Primary Examiner*—Robert D. Budens
*Attorney, Agent, or Firm*—Morrison & Foerster, LLP

[57] ABSTRACT

Monoclonal antibodies to transforming growth factor beta (TGF-B) are prepared from hybrid cell lines by immunizing with TGF-B2. The antibodies may be of any isotype and may be of any mammalian origin such as murine or human origin. Therapeutic applications utilizing the TGF-B monoclonal antibody are also disclosed.

7 Claims, 5 Drawing Sheets

OTHER PUBLICATIONS

Lee et al., "β transforming growth factors are potential regulators of B lymphopoiesis" *J. Exp. Med.* (1987) 166:1290–1299.

Ohta et al., "Two forms of transforming growth factor–β distinguished by multipotential hematopoietic progenitor cells" *Nature* (1987) 329;539–541.

Ranges et al., "Inhibition of cytotoxic T cell development by transforming growth factor β and reversal by recombinant tumor necrosis factor alpha" *J. Exp. Med.* (1987) 166:991–998.

Rook et al., "Effects of transforming growth factor β on the functions of natural killer cells depressed cytolytic activity and blunting of interferon responsiveness" *J. Immunol.* (1986) 136:3916–3920.

Rosa et al., "Mesoderm induction in amphibians the role of TGF–β–2–like factors" *Science* (1988) 239:783–785.

Seyedin et al., "Cartilage–inducing factor β is a unique protein structurally and functionally related to transforming growth factor–β" *J. Biol. Chem.* (1987) 262:1946–1949.

Sing et al., "Transforming growth factor β selectively inhibits normal and leukemic human bone marrow cell growth in–vitro" *Blood* (1988) 72:1504–1511.

Wahl et al., "Transforming growth factor type β induces monocyte chemotaxis and growth factor production" *Proc. Natl. Acad. Sci. USA* (1987) 84:5788–5792.

Flanders et al., "Antibodies to peptide determinants in transforming growth factor β and their applications" *Biochem.* (1988) 27:739–746.

Massaguè, "The TFG–β family of growth and differentiation factors" *Cell* (1987) 49:437–438.

Testa et al., "The biology of long–term bone marrow cultures and its application to bone marrow transplantation" *Curr. Opinion Oncol.* (1991) 3:272–278.

Berenson et al., "Engraftment after infusion of CD34$^+$ marrow cells in patients with breast cancer or neuroblastoma" *Blood* (1991) 77:1717–1722.

Eaves et al., "In vitro culture of bone marrow cells for autografting in CML" *Leukemia* (1993) 7:S126–S129.

Waegell et al., "Growth acceleration and stem cell expansion in Dexter–type cultures by naturalization of TGF–β" *Experimental Hematology* (1994) 22:1051–1057.

Durum et al.., "Proinflammatory Cytokines and Immunity," in *Fundamental Immunology*, 3rd Ed., Paul, W.E., Ed., Raven Press, Ltd., New York, 1993.

MONOCLONAL ANTIBODIES TO TRANSFORMING GROWTH FACTOR-BETA AND METHODS OF USE This application is a division of application Ser. No. 07/759,109, filed Sep. 6, 1991, now U.S. Pat. No. 5,571,714, which is a continuation of application Ser. No. 07/288,432, filed Dec. 22, 1988, now abandoned.

FIELD OF THE INVENTION

The present invention relates to the field of immunology and particularly to monoclonal antibodies specific to transforming growth factor beta (TGF-B) and applications thereof.

BACKGROUND OF THE INVENTION

Transforming growth factor beta (TGF-B) is a family of related multifunctional regulators of cell growth which can affect cellular proliferation and differentiation. Two forms of TGF-B, TGF-B1 and TGF-B2, are, in general, multifunctional cytokines that have potent inhibitory effects on the proliferation and effector responses of mitogen-, lymphokine-, and alloantigen-activated lymphocytes (Kearl et al, *J Exp Med* (1986) 163:1037; Ellingsworth et al, *Cell Immunol* (1988) 113: in press; Kearl et al, *J Immunol* (1986) 137:3855; Ranges et al, *J Exp Med* (1987) 166:991). In addition, TGF-B1 and TGF-B2 affect the proliferation and differentiation of other cells of the immune system including macrophages (Wall et al, *Proc Natl Acad Sci USA* (1987) 84:5788), pre-B cells (Lee et al, *J Exp Med* (1987) 166:1290), hemato-poietic stem cells (Ohta et al, *Nature* (1987) 329:539; Ishibashi et al, *Blood* (1987) 69:1737; Keller et al, *J Exp Med* (1988) in press; Sing et al, *Blood* (1988) in press), and NK cells (Rook et al, *J Immunol* (1986) 136:3916).

The generation of immunoprecipitating and neutralizing antibodies to native TGF-B has been extremely difficult due to the highly conserved nature of native TGF-B among different species. The human sequence of TGF-B1 is identical to the bovine and porcine sequences and differs from the murine sequence by one amino acid TGF-B1 is a dimer composed of two identical disulfide-linked chains of 112 amino acid residues.

TGF-B2 is also a dimeric polypeptide and is disclosed in U.S. Pat. No. 4,774,322, filed 10 Dec. 1987, assigned to Collagen Corporation. Even though there are 14 amino acid differences in the first 36 amino acids residues of the two forms, their biological activities are similar (Cheifetz et al, *Cell* (1987) 48:409–415; Seyedin et al, *J Biol Chem* (1987) 262:1946–1949).

Western blots and immunohistochemical localization studies on TGF-B1 have been performed using a polyclonal rabbit antiserum obtained by immunization with a synthetic peptide corresponding to the $NH_2$-terminal 30 amino acids of TGF-B1 (Ellingsworth et al, *J Biol Chem* (1986) 261:12362). Polyclonal antisera to human and porcine TGF-B (Keski-Oja et al, *Cancer Res* (1987) 47:6451–6458) and to porcine TGF-B2 (Rosa et al, *Science* (1988) 239:783–785) have been shown to neutralize the biological activity of TGF-B1 and TGF-B2, respectively. Monoclonal antibodies specific to TGF-B have not been previously described. The availability of these specific antibodies is important for characterization of the role played by TGF-B in the immune system and other physiological processes.

Antibodies to TGF-B are needed to investigate the varied biological actions of TGF-B, to study TGF-B biosynthesis, and to determine differences in activity or effect, if any, between the forms of TGF-B. These antibodies would also have therapeutic applications for treating indications where there is an overproduction of TGF-B (e.g., acute liver injury, chronic hepatic fibrosis) and for diagnosing or treating malignancies (e.g., sarcomas and melanomas) and metastatic cancers.

SUMMARY OF THE INVENTION

The present invention provides a monoclonal antibody immunoreactive with TGF-B. A monoclonal antibody is described herein that is specific for TGF-B. This antibody, in preferred embodiments, binds to a neutralizing epitope on TGF-B or binds to an epitope on TGF-B which blocks the binding of TGF-B to its cellular receptors.

Another aspect of the invention is to provide a stable cell line which secretes a monoclonal antibody specific for TGF-B. In one embodiment of the invention, the cell line secretes a murine monoclonal antibody specific for TGF-B that has TGF-B neutralizing activity.

Another aspect of the invention is a method for treating acute and chronic disease states that result from an overproduction of TGF-B, by administering a therapeutically effective amount of a monoclonal antibody reactive with TGF-B, or an antigen-binding fragment of a monoclonal antibody reactive with TGF-B.

Another aspect of the invention is a method for treating tumor cells that produce TGF-B, by administering a therapeutically effective amount of a monoclonal antibody reactive with TGF-B to suppress the immunosuppressive effects of TGF-B.

Another aspect of the invention is a method for treating metastatic cancers by administering a therapeutically effective amount of a monoclonal antibody reactive with TGF-B to mark tumor cells for destruction by complement or by immune cells dedicated to tumor cell removal.

Another aspect of the invention is a capture-ELISA (CELISA) for diagnosing disease states such as cancer and connective tissue (fibrotic) disorders comprising: coating a first monoclonal or polyclonal antibody reactive with TGF-B onto a surface, adding a sample containing an unknown amount of TGF-B or a standard concentration of purified TGF-B to the surface, adding polyclonal sera reactive with TGF-B or a monoclonal antibody of the invention to the surface, adding an enzyme-linked tertiary antibody (reactive to said monoclonal or polyclonal antibody), and determining the presence of TGF-B by quantifying the amount of enzymatic label present in a colorimetric reaction.

Another aspect of the invention is a chimeric monoclonal antibody, having an antigen-binding portion derived from the MAb of the invention, and the remainder derived from human antibodies. Such chimeric antibodies are described by S. L. Morrison, *Science* (1985) 229:1202.

Another aspect of the invention is an anti-idiotypic antibody reactive with the MAbs of the invention, which are useful as TGF-B mimics. These mimics are capable of binding to TGF-B receptors, and thus may act as TGF-B agonists or antagonists.

These and other objects and features of the invention will become more fully apparent from the following detailed description of the invention.

MODES OF CARRYING OUT THE INVENTION

Figure 1:
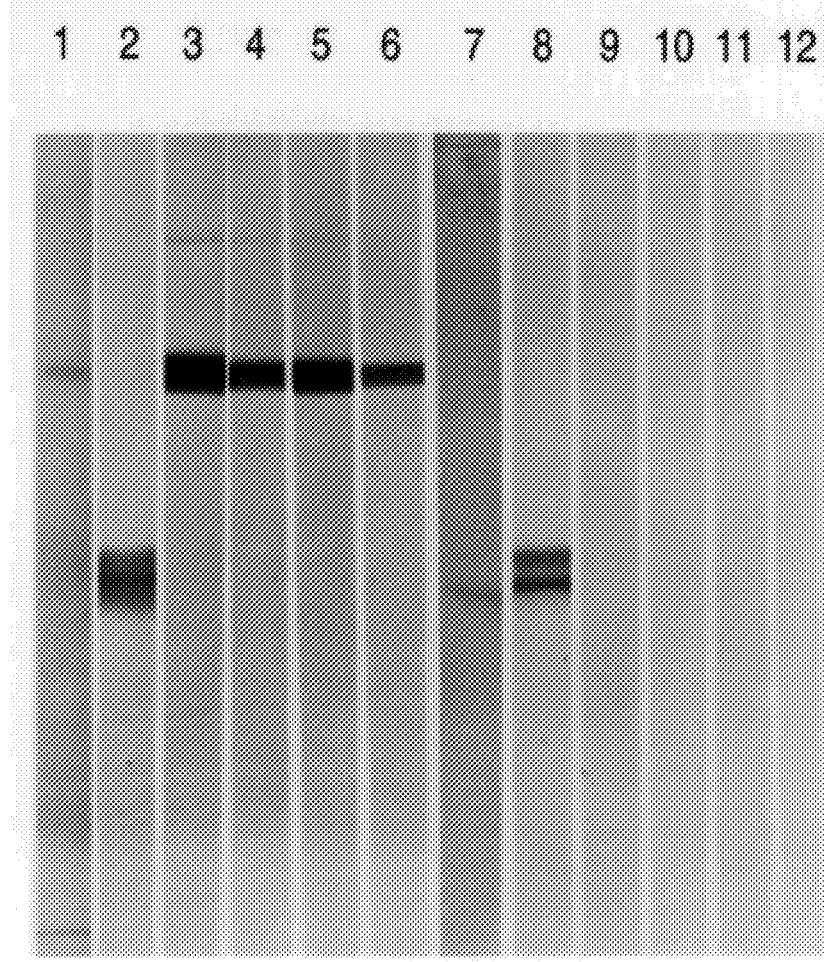
FIG. 1 is a Western blot of monoclonal antibodies binding to purified TGF-B2. Lanes 1–6 and 7–12 contain TGF-B2 run under non-reducing and reducing conditions, respectively.

The present invention is directed broadly to the production of TGF-B monoclonal antibodies, neutralizing TGF-B antibodies and TGF-B antibodies that block the binding of TGF-B to cellular receptors. The present invention is also directed to the use of such antibodies in diagnostic assays to determine elevated levels of TGF-B that are associated with certain disease states, and in therapeutic applications to prevent the overproduction of TGF-B or to suppress the immunosuppressive effects of TGF-B in tumor cells.

A. Definitions

As used herein the terms "monoclonal antibody" and "MAb" refer to an immunoglobulin composition having a substantially homogenous population of antibodies, each of which binds to the same antigenic determinant. Unless otherwise indicated, the term is not intended to be limited to antibodies of any particular mammalian species or isotype, or to antibodies prepared in any given manner The term is intended to include whole antibody molecules as well as antigen-binding fragments (e.g., Fab', F(ab')$_2$).

"Cell line" refers to various embodiments including but not limited to individual cells, harvested cells, and cultures containing cells so long as they are derived from cells of the cell line referred to.

As used herein with respect to characterizing the claimed hybrid cell lines, the terms "permanent" and "stable" mean that the lines remain viable over a period of time, typically at least about six months, and maintain the ability to produce the specified monoclonal antibody through at least about 50 passages.

"TGF-B" refers in general to the family of transforming growth factors (beta-chain) which participate in the control of cell proliferation and differentiation. As used herein the term refers to both TGF-B1 and TGF-B2 proteins. Other known TGF-B-like proteins are the "inhibins" (Mason et al, Nature (1985) 318:659–663), their beta-chain dimers, "activins" (Ling et al, Nature (1986) 321:779–782; Vale et al, Nature (1986) 321:776–779), Mullerian inhibiting substance (Cate et al, Cell (1986) 45:685–698) and a predicted protein product of the decapentaplegic gene complex of Drosophila (Padgett et al, Nature (1987) 325:81–84) as shown by complementary DNA sequence analysis.

An antibody that "is reactive with" or "specific to" TGF-B is an antibody that binds an epitope present on TGF-B.

An antibody that "neutralizes in vitro biological activity of TGF-B" when bound to its epitope on TGF-B is defined by testing the antibody-bound TGF-B in an in vitro assay such as the IL-1 and PHA-dependent thymocyte proliferation assay, the NRK proliferation assay or an assay using the ROS 17.2.8 osteosarcoma cell line, all of which are described in the following examples An antibody that "blocks binding to cellular receptors" of TGF-B is an antibody that blocks the binding of TGF-B to TGF-B cellular receptors in a standard receptor binding assay, such as the one described in the examples below. Cells which are known to have TGF-B cellular receptors include mouse thymocytes (C3H/HeJ) and the NRK cell line (clone 49F, ATCC CRL 1570).

The term "binding affinity" or K$_a$" of an antibody to its epitope, as used herein, refers to a binding affinity that may be calculated according to standard methods by the formula K$_a$=8/3 (It-Tt) where It is the total molar concentration of inhibitor uptake at 50% tracer and Tt is the total molar concentration of tracer. See Muller, $J$ $Immunol$ $Meth$ (1980) 34:345–352. Binding affinity may also be calculated using the formula B/T=n·N$_{Ab}$·W·[(V-V$_m$)K+Q·W]. See Antoni and Mariani, $J$ $Immunol$ $Meth$ (1985) 83:61.

The term "therapeutically effective amount" as used herein refers to the amount of antibody that neutralizes the biologic activity of TGF-B, which may be measured by either (1) a pathologic evaluation of the prevention of fibrosis, or (2) an inhibition of the immunosuppressive effects of TGF-B which results in tumor regression.

The general procedures of producing monoclonal antibodies, including the cell lines which produce such compositions, are well known in the art. See, e.g., Gerhard et al, $Proc$ $Natl$ $Acad$ $Sci$ $USA$ (1978) 75:1510; $Monoclonal$ $Antibodies$ (R. Kennett, T. McKearn, & K. Bechtol eds. 1980); $Monoclonal$ $Antibodies$ $and$ $T$-$Cell$ $Hybridomas$ (G. Hammerling, U. Hammerling, & J. Kearney eds. 1981); Kozbor et al, $Proc$ $Natl$ $Acad$ $Sci$ $USA$ (1982) 79:6651; Jonak et al, $Hybridoma$ (1983) 2:124; $Monoclonal$ $Antibodies$ $and$ $Functional$ $Cell$ $Lines$ (R. Kennett, K. Bechtol, & T. McKearn eds. 1983); Kozbor et al, $Immunology$ $Today$ (1983) 4:72–79; Shulman et al, $Nature$ (1982) 276:269–270; Oi et al, $in$ $Selected$ $Methods$ $in$ $Cellular$ $Immunology$, pp. 351–371 (B. Mishell & S. Schiigi eds. 1980); and Foung et al, $Proc$ $Natl$ $Acad$ $Sci$ $USA$ (1983) 79:7484–7488.

In a preferred embodiment, anti-TGF-B antibody-producing primary B cells are isolated from a mammal immunized with TGF-B and then immortalized so that a cell line can be established. Any appropriate technique of immortalizing the primary B cells can be employed, including, but not limited to, fusion with a myeloma cell, transformation with oncogenic DNA, or transfection with Epstein-Barr virus. Preferred myeloma cells for this purpose are those which do not themselves secrete immunoglobulins, which fuse efficiently, support stable high-level expression of antibody by the selected antibody-producing cells, and are sensitive to selection mediums such as HAT medium. Among these, presently preferred myeloma cell lines are murine myeloma lines such as those derived from P3X63-Ag8.653 (653) and Sp2/0-Ag14 (SP2/0) myeloma lines available from the American Type Culture Collection, Rockville, Md., under ATCC CRL Nos. 1580 and 1581, respectively.

Immortalized cells, such as the murine hybridomas, a re screened for production of the desired anti-TGF-B antibodies having the appropriate affinity and/or epitope. A particularly useful screen for regularly isolating high affinity antibodies is to screen antibodies using a solid phase radioimmune assay (RIA). Generally, monoclonal antibodies having binding affinities for TGF-B of at least about $10^7$ M$^{-1}$ are selected. The present invention regularly permits the isolation of antibodies with binding affinities of at least about $10^7$ M$^{-1}$ to about $10^8$ M$^{-1}$.

The present invention is also directed to anti-TGF-B monoclonal antibodies that neutralize the in vitro inhibitory effects of TGF-B. Screening monoclonal antibodies for this ability can be in addition to the screen for high binding affinity. In general, standard in vitro neutralization assays may be employed in this screen. In a preferred embodiment of the present invention, the MAb 1D11.16 is found to neutralize both TGF-B1 and B2 activity. This suggests that a conserved portion of both molecules serves as the MAb binding epitope, and that this epitope is either within or close to the cell receptor binding site of TGF-B. Work by Flanders et al, *Biochem* (1988) 27:739–746 with polyclonal antisera raised against synthetic peptides corresponding to different regions of TGF-B1 implicated the C-terminal portion of TGF-B1 in receptor binding. Comparison of the C-terminal sequences of TGF-B1 and B2 reveals only 7 differences in the final 30 amino acid residues of the molecules. Since the most highly conserved portion of the molecules is actually between residues 20 and 44, it appears possible that this region is a target for the cell receptor binding site on TGF-B.

Several preferred murine monoclonal antibodies have been produced according to the present invention. Monoclonal antibody 1D11.16 (IgG1) refers to the MAb produced by a clone of the murine hybridoma cell line 1D11.16. Samples of this cell line were deposited with the American Type Culture Collection (ATCC), 12301 Parklawn Drive, Rockville, Md. Cell line 1D11.16 was assigned ATCC HB9849, and is guaranteed to be publicly available for thirty years after the issue date of this patent. Monoclonal antibodies produced by the clones of this cell line may be distinguished using the Western Blot Assay, wherein the antibody MAb 1D11.16 would recognize both TGF-B1 and TGF-B2. The antibodies of the present invention may be used to treat acute or chronic fibrosis that is associated with overproduction of TGF-B. The body responds to injury or disease by regenerating destroyed tissue. When the injury or disease is prolonged or extensive, the destroyed tissue may be replaced by specialized fibrotic connective tissue. Excess deposition of this fibrotic tissue may result in an impairment of the affected tissue or organ function, and in some instances may be disfiguring to the patient. It is currently believed that there is an overproduction of TGF-B in diseases such as interstitial lung fibrosis, liver cirrhosis, and fibrotic skin disorders such as scleroderma and scarring: M. J. Czaja et al, *J Cell Biol* (1988) (in press); D. G. Hoyt et al, *J Pharm Exp Ther* (1988) 246:765. A therapeutically effective amount of the antibody of this invention may be administered to neutralize the biologic activity of TGF-B, which in turn would result in prevention of unwanted fibrosis.

It is also generally known that TGF-B is produced by different tumor cells (sarcomas and carcinomas). This production may protect the tumor cells from recognition by the host's immune system: M. Wrann et al, *EMBO J* (1987) 6:1633. In these situations, TGF-B suppresses the proliferation of T and B cells, NK cells, LAK cells, and macrophages that are involved in tumor destruction. The MAb of this invention may be administered to block TGF-B's immunosuppressive effects (to permit the generation of an immune response against the tumor), and result in tumor regression.

The antibody of the invention neutralizes the biological activity of TGF-B by preventing the antigen from binding to its cell surface receptors. The intact antibody, antigen binding fragments (e.g., Fab', F(ab')$_2$), or chimeric antibodies may be useful in these applications. In addition, administration of the antibodies of the invention would form immune complexes (antigen-anti-body complexes) that will increase the rate at which the antigen TGF-B, is cleared from systemic circulation or from the tissue site where the antigen is produced.

These types of fibrotic diseases and tumor cells may be treated by administering a therapeutically effective amount of the antibodies of the invention to affect the inhibition of fibrosis formation or regression of tumor cells. The method and frequency of administration, the dose range, and the duration of the antibody therapy will vary with the severity and nature of the condition, and the general health of the patient.

In a preferred embodiment, the antibodies of the invention are administered locally to the affected tissue sites by bolus injection or perfusion. The amount of antibody administered may be measured by maintaining the local tissue concentration of TGF-B at about 1–1,000 ug/mL.

Indications where this mode of treatment is particularly useful are for the control of excessive scar tissue formation, due to surgery or trauma, or prevention of the formation of connective tissue adhesions. For treatment of tumor cells by local administration, the antibodies may be delivered directly into a tumor mass through a vascular catheter for deep solid tumors, or through a hypodermic needle for superficial or cutaneous tumors. The antibodies may be locally administered by a single bolus injection that is repeated over several days, or by continuous administration by perfusion. The amount of antibody administered is preferably about 1 ug to 1,000 ug per gram tumor tissue.

In another preferred embodiment, the antibodies of the invention may be administered systemically by intravenous or peritoneal perfusion, or by bolus injection into the subcutaneous tissue or muscle. The antibodies may be delivered in vehicles generally known to those skilled in the art, such as saline, balanced salt solutions, isotonic or phosphate buffered saline (pH 7), with or without dextrose. The amount of antibody administered may be measured by maintaining the circulating serum concentration between about 1 ug to 5 mg per mL serum.

Indications where this mode of treatment is particularly useful are systemic diseases such as interstitial lung fibrosis, liver cirrhosis, scleroderma, and metastatic cancer.

For both local and systemic treatment, the antibodies of the invention may be administered in combination with other antibodies reactive with TGF-B to reduce the amount of bioavailable factor.

The antibodies of the present invention may also be used in a number of immunoassays, including assays to purify or quantify TGF-B. For example, in one embodiment, a monoclonal antibody reactive with TGF-B, such as 1D11.16, is coated onto microtiter wells. This antibody will capture any TGF-B present in a solution of unknown proteins. The captured TGF-B is then recognized by a second polyclonal antibody that also recognizes TGF-B. The second antibody is preferably of a different subclass or species than the first antibody, to allow the specific recognition of the second antibody by a third antibody (e.g., goat anti-rabbit IgG) that is coupled to peroxidase. Thus, in this assay, color development only occurs when TGF-B binds to the capturing antibody 1D11.16. The amount of TGF-B in an unknown solution is quantified by comparison of color development to a standard dilution curve of known amounts of TGF-B. High levels of TGF-B are indicative of the presence of fibrotic disease or tumor mass.

The following examples are presented for illustrative purposes only and are not to limit the scope of the present invention. Variations in the source, type, and method of producing antibodies will be apparent to those of ordinary skill in the art, and may be employed without departing from the scope of the present invention.

EXAMPLE 1

(Purification of Bovine TGF-Bs)

Bone derived TGF-B1 and B2 were purified from the noncollagenous, guanidine-HCI soluble protein fractions of demineralized bovine metatarsal bone These factors were purified by a combination of gel filtration, CM-cellulose cation exchange chromatography and C18:reverse phase high pressure liquid chromatography (HPLC) using a previously described method (Seyedin et al, *Proc Natl Acad Sci USA* (1985) 82:2267). Protein concentrations were determined spectrophotometrically by comparison of absorbance at $OD_{210}$ to a solution of protein of known concentration.

EXAMPLE 2

(Immunization of Mice and Fusion Procedure)

A group of female Balb/c mice was injected intraperitoneally (IP) with 10 ug of native bovine TGF-B2 with complete Freund's adjuvant (Sigma Chemical Co., St. Louis, Mo.). At 3 week intervals, the animals were boosted with 10 ug of TGF-B2 in incomplete Freund's adjuvant (Sigma). Following the second boost, the mice were bled and serum antibody titers against TGF-B2 checked by ELISA. The animal with the highest titer (recip. dil.=5120) was given a final intravenous (IV) injection of TGF-B2 three weeks after the last IP boost and sacrificed for use in the fusion process. For all injections, the TGF-B2 was lyophilized with carrier mouse serum albumin (10 ug albumin per ug TGF-B2) prior to solubilization and injection.

Fusion to the SP2/0 myeloma (GM3659 B, NIGMS Human Genetic Mutant Cell Repository, Camden, N.J.) was performed 4 days after the IV challenge. The fusion was performed essentially according to the protocol of Oi and Herzenberg, "Immunoglobulin-producing hybrid cell lines" in *Selected Methods in Cellular Immunology*, Mishell and Shiigi, eds., W. H. Freeman and Co., San Francisco, pp. 357–362, (1980). Spleen cells were mixed with SP2/0 at a ratio of 5:1 ($2.2 \times 10^8$ splenocytes: $4.4 \times 10^7$ SP2/0 cells). 50% polyethylene glycol 1500 (Boehringer-Mannheim Biochemicals, Indianapolis, Ind.) was used as the fusagen. Cells were plated at $10^6$ cells/well along with resident peritoneal cells at $4 \times 10^3$ cells/well in DMEM with high glucose (4.5 g/l) supplemented with 20% FCS (Hyclone Laboratories, Logan, Utah), 2 mM L-glutamine, 2 mM sodium pyruvate, nonessential amino acids, penicillin and streptomycin. In this procedure, aminopterin was replaced by azaserine (Sigma) according to the procedure by Larrick et al, *Proc Natl Acad Sci USA* (1983) 80:6376, and added along with thymidine and hypoxanthine on day 1 after the fusion. In this fusion, virtually every well contained selection-resistant colonies that were screened for anti-TGF-B2 MAb production by ELISA. All wells positive for TGF-B2 MAb were cloned by limiting dilution.

EXAMPLE 3

(ELISA Assay)

The ELISA for TGF-B2 was performed according to standard procedures (Ellingsworth et al, *J Biol Chem* (1986) 261:12362; Engvall and Perlmann, *J Immunol* (1972) 109:129). Briefly, wells of a 96 well microtiter plate (Immulon, Dynatech Laboratories, Alexandria, Va.) were coated overnight with 0.25 ug/well of TGF-B2 in a 0.01M carbonate coating buffer (pH 9.6). For ELISAs done with TGF-B2 peptides, 2.5 µg/well of peptide was coated onto plates overnight. Plates were washed with PBS (pH 7.4) containing 0.05% Tween® 20 (J. T. Baker, Phillipsburg, N.J.) (PT buffer). Plates were blocked with PT containing 1% (w/v) gelatin for 60 min at room temperature. After addition of culture supernatants or purified antibody for 60 min, plates were washed and incubated with 2nd step antibody (peroxidase-conjugated goat anti-mouse IgG, Southern Biotechnology, Birmingham, Ala.). After an additional 60 min, plates were washed and incubated with a one component peroxidase substrate solution (ABTS) (Kirkegaard and Perry, Gaithersburg, Md.). Plates were read with a titretek Multiscan MCC ELISA reader (Flow Laboratories, McLean, Va.). Identification of MAb subclasses was accomplished by ELISA as taught above, except that sub-class specific secondary Abs were employed (rat anti-mouse MAb-peroxidase conjugates, Zymed, South San Francisco, Calif.).

Table I below summarizes some of the characteristics of each of these MAbs. Of particular interest are the relative affinity measurements of the binding of the MAb to TGF-B2 as assessed by a solid phase competitive RIA. The MAb 1D11.16 exhibits the highest affinity for TGF-B2. However, the affinities of all the MAb are relatively similar. Also of interest is the fact that only one of the MAbs, 1D11.16, cross-reacts with TGF-B1 by ELISA.

TABLE I

Properties of Anti-TGF-B Monoclonal Antibodies

| MAb | Subclass | X-reacts with B1 | Neutralizing Activity | Relative Affinity | Imppt. |
|---|---|---|---|---|---|
| 3C7.14 | 2B | – | – | +++ | ++++ |
| 1D11.16 | 1 | + | + | ++++ | ++ |
| 2G1.1.12 | 1 | – | – | ++ | +++ |
| 2D7.20 | 2A | – | – | + | + | a Subclasses were determined by ELISA.
b Cross-reactions were determined by ELISA with TGF-B1 coated plates.
c Neutralization was determined in the I1–1, PHA-dependent thymocyte assay (see FIG. 2).
d Affinity constants were determined by solid phase RIA and nonlinear regression analysis. Four + indicates MAb with highest affinity. Ka determined from three experiments are as follows: 1D11.16, $3.4 \times 10^8$ L/mol; 3C7.14, $1.9 \times 10^8$ L/mol; 2G1.1.12, $1.6 \times 10^8$ L/mol; and 2D7.20; $1.6 \times 10^7$ L/mol.
e Immunoprecipitation was performed by mixing [$^{125}$I]-labeled TGF-B2 with MAb and followed by addition of anti-Ig-agarose (see FIG. 3). Four + indicates MAb with highest precipitating capability.

Mapping of the epitopes recognized by the MAbs was attempted by running ELISAs with synthetic peptides corresponding to portions of TGF-B2 as coating antigens. Three peptides were tested: 1–29, 47–76, 79–108. None of the MAbs were found to bind appreciably to the synthetic peptides even though a 30-fold molar excess of peptide was coated relative to the amount of TGF-B2 normally coated onto plates. A possible explanation for this result may be provided by the Western analysis (see below). In the Westerns, only the MAb 2G1.1.12 weakly recognized the reduced monomeric form of the molecule.

EXAMPLE 4

(Western Blots)

This protocol follows standard procedures (Ellingsworth et al, (1986) *supra*; Towbin et al, *Proc Natl Acad Sci USA* (1979) 76:4350. TGF-B2 was electro-phoresed in a 15% SDS polyacrylamide gel. The protein was then transferred to nitrocellulose in a high pH transfer buffer (25 mM Tris, 192 mM glycine, pH 11; with 20% methanol). After overnight transfer in a Bio-Rad transfer apparatus (170 mA constant current), the blot was blocked with 2.5% non-fat dry milk in PT (PT-BLOTTO). The nitro-cellulose strips were incubated with MAb-containing supernatants or purified IgG in PT-BLOTTO for 60 min. After washing, the strips were incubated with the previously-described 2nd step antibody (peroxidase-conjugated goat anti-mouse IgG) for an additional 60 min. The presence of antibody was visualized by addition of the peroxidase substrate: 0.06% (w/v) 4-chloro-1-napthol (Sigma-) and 0.01% hydrogen peroxide in 0.05M Tris-buffered saline (pH 7.4). The reaction procedure was halted by extensive washing of the blot in deionized $H_2O$.

FIG. 1 illustrates the Western blot pattern of the binding of the four MAbs to native bovine TGF-B2. Lanes 1–6 and 7–12 contain TGF-B2 run under non-reducing and reducing conditions, respectively. Lanes 1 and 7 are amido black stained TGF-B2. Lanes 2–6 and 8–12 were incubated respectively with the following antibodies: lanes 2 and 8, 2F9.15; lanes 3 and 9, 3C7.14; lanes 4 and 10, 1D11.16; lanes 5 and 11, 2D7.20; and lanes 6 and 12, 2G1.1.12. The monoclonal 3C7.14 is the strongest reactor with TGF-B2 in these blots. Although not visible on the gel, MAb 2G1.1.12 reacted very slightly with reduced monomeric TGF-B2; none of the other MAbs are able to bind appreciably to reduced monomeric TGF-B2 (lanes 9–12). Also included in lanes 2 and 8 is the reactivity pattern of an additional MAb that recognizes a protein contaminant present in the biochemically purified TGF-B2 preparations. This pattern is representative for several other MAbs produced that also recognize this identical contaminant (data not presented). On silver staining of PAGE gels, this contaminant was found to represent a small percentage of the immunizing protein.

Figure 5:
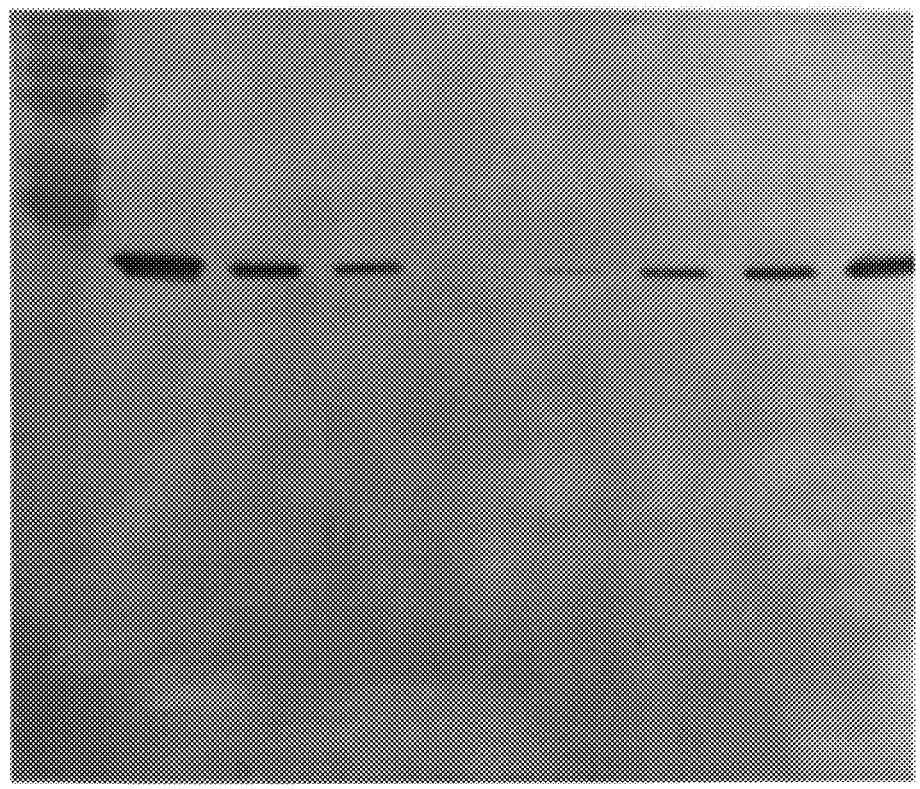
FIG. 5 is a Western blot of monoclonal antibody 1D11.16 binding to purified TGF-B1 and TGF-B2. Lanes 2–5 and 6–9 contain various amounts of TGF-B2 and TGF-B1, respectively, run under non-reducing conditions.

FIG. 5 illustrates the binding of MAb 1D11.16 to both TGF-B1 and TGF-B2 under non-reducing conditions. Lanes 2–5 and 6–9 contained various amounts of TGF-B2 and TGF-B1, respectively. The amounts were 1 ug/lane (lanes 2 and 9), 0.25 ug/lane (lanes 3 and 8), 0.1 ug/lane (lanes 4 and 7), and 0.025 ug/lane (lanes 5 and 6). The lack of reactivity in lane 5 is believed to be an artifact due to loss of the sample during lyophilization prior to running the SDS gel.

EXAMPLE 5

(Neutralization of Bioactivity)

The IL-1 and PHA-dependent thymocyte assay for TGF-B described in Ellingsworth et al, *Cell Immunol* (1988) 114:41 was employed. In these experiments, either 50 or 100 ul of MAb-containing culture supernatant or purified IgG diluted in medium was added to the cultures at the same time as TGF-B1 or B2. The TGF-B concentrations were employed over a range of $10^{-12}$ to $10^{-10}$M.

Figure 2:
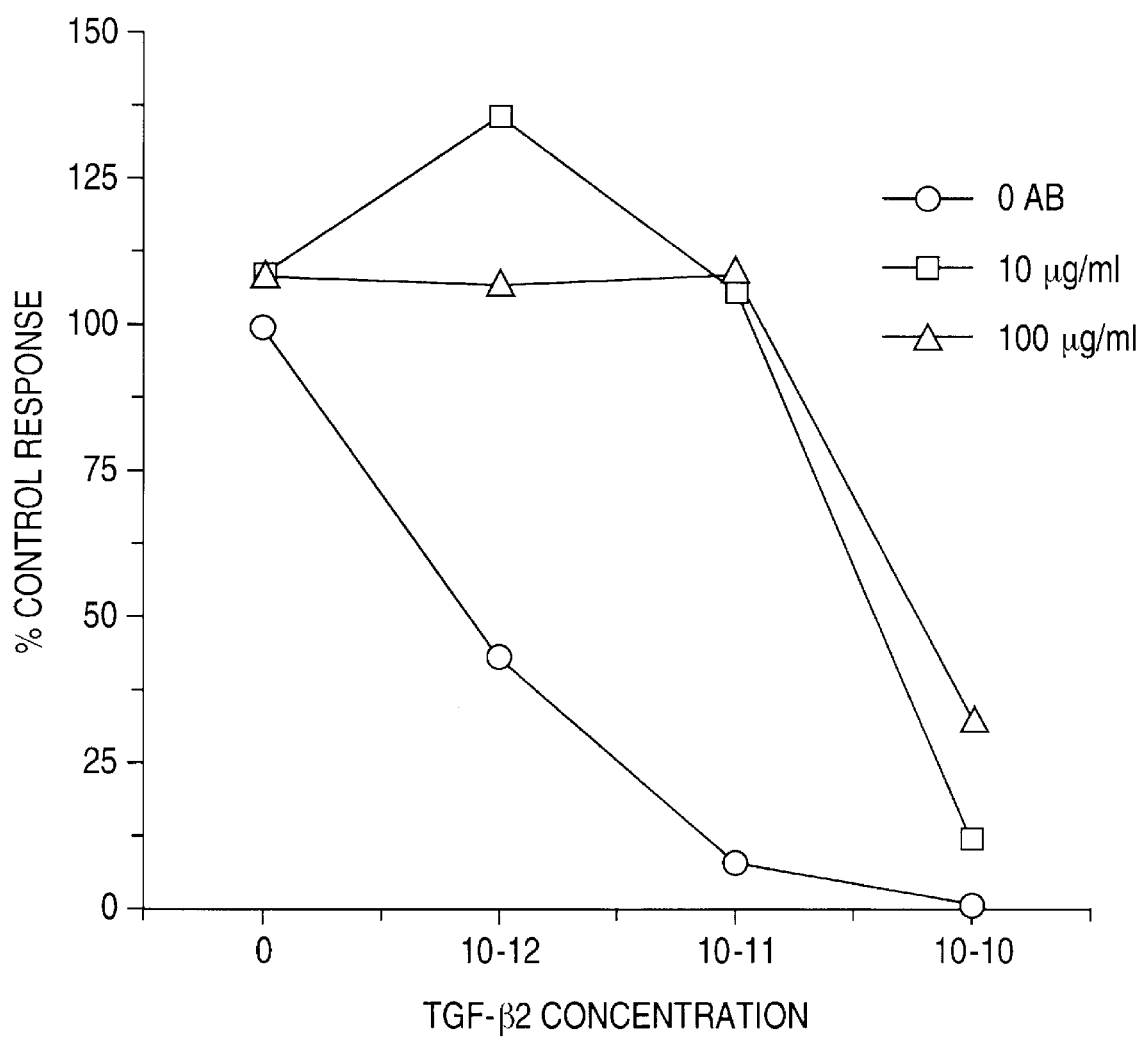
FIG. 2 illustrates the neutralization of TGF-B2 activity by the 1D11.16 MAb.

Preliminary experiments showed that only one of the four MAbs, 1D11.16, was able to neutralize the inhibitory effects of TGF-B. FIG. 2 shows the ability of affinity purified 1D11.16 to neutralize the anti-proliferative actions of TGF-B. This figure demonstrates that the IL-1 and PHA-dependent proliferation of thymocytes is inhibited by TGF-B2 over a concentration range of $10^{-12}$ to $10^{-10}$M. Addition of 10 or 100 ug/mL 1D11.16 will effectively neutralize $10^{-11}$M TGF-B2 when both TGF-B2 and antibody are added at the start of culture. 1D11.16 is also found to neutralize the activity of TGF-B1 to a similar extent in this assay. This suggests that a similar epitope on both TGF-B1 and B2 is recognized by the neutralizing antibody and that this epitope may be within or adjacent to the receptor binding site on TGF-B. 1D11.16 is able to neutralize the growth promoting actions of TGF-B1 and B2 in the NRK proliferation assay (Roberts et al, "Purification of type B transforming growth factors from non-neoplastic tissues" in *Cell Culture Methods for Molecular and Cell Biology*, Barnes et al, eds., Ed. Alan Liss, Inc., New York pp. 181–194, (1984)) and to neutralize TGF-B induced alkaline phosphatase production in an assay using the ROS 17.2.8 osteosarcoma cell line (obtained from Dr. Greg Mundy, U. Texas Health Science Center, San Antonio, Tex.). These results suggest that a single receptor binding domain is present in TGF-B1 and B2 and that this binding domain appears to be responsible for the pleiotropic actions attributed to TGF-B1 and B2.

EXAMPLE 6

(Inhibition of Receptor Cross-linking by 1D11.16)

The cross-linking of $[^{125}I]$-labeled TGF-B1 and B2 to its cellular receptors employs the methods described in Ellingsworth et al (1986) *supra* and Segarini et al, *J Biol Chem* (1987) 262:14655. In the current experiments, either 1D11.16 antibody (30 ug/mL) or a non-TGF-B-reactive mouse MAb at an equivalent concentration was pre-mixed with $[^{125}I]$-labeled TGF-B1 or B2 (50 pM final concentration) for 60 min prior to addition to the cells The cells employed in the assay were freshly isolated mouse thymocytes (C3H/HeJ) and the NRK cell line (clone 49F, CRL 1570).

Figure 3:
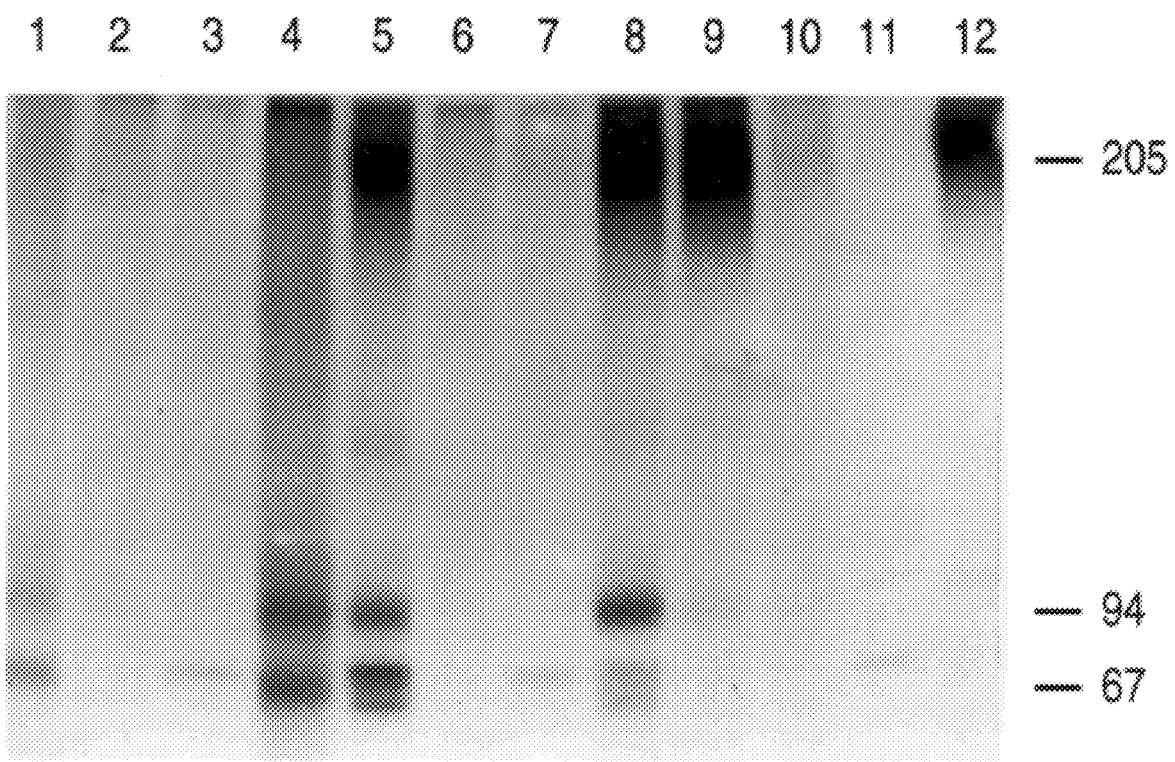
FIG. 3 represents an autoradiogram showing inhibition of affinity cross-linked cell receptors from both thymocytes and the NRK cell line by MAbs.

The ability of the MAb 1D11.16 to block the cross-linking of $[^{125}I]$-labeled TGF-B by addition of disuccinimidyl suberate (DSS) to its cell surface receptor complex was assessed. The receptor complex consists of three major species that have approximate molecular weights of 65 kilodaltons (Kd), 85–95 Kd, and 200–280 Kd. FIG. 3 represents an autoradiogram of TGF-B cross-linked cell receptors from both thymocytes and the NRK cell line. Approximately $1\times10^7$ thymocytes (lanes 1–4) or $5\times10^6$ NRK cells (lanes 5–12) were used. Lanes 2 and 6 received 20 nM non-labeled TGF-B1 and lane 10 received 20 nM unlabeled TGF-B2 to show the specificity of binding. Lanes 3, 7 and 11 received 1D11.16 MAb. The addition of control mouse IgG (negative control, lanes 4, 8 and 12) did not affect TGF-B binding to its receptors. Binding of both TGF-B1 and TGF-B2 to the cellular receptors is effectively inhibited by the MAb 1D11.16 (lanes 3, 7, and 11). Only the binding to the 65 Kd receptor is not completely blocked by the antibody. The ability of both the high molecular weight receptor and the lower molecular weight receptors to be inhibited suggests that the binding epitope on TGF-B for these receptors is similar. Since the MAb 1D11.16 blocks binding to all receptors, one is not able to distinguish between the receptors with respect to function.

EXAMPLE 7

(Immunoprecipitation of Iodinated TGF-B2)

The ability of the different MAbs to precipitate iodinated TGF-B2 was assessed. TGF-B2 was labeled with $[^{125}I]$-TGF-B2 by the chloramine T method (Frolik et al, *J Biol Chem* (1984) 259:10995). 200 ul of MAb-containing culture supernatant or purified IgG in 0.02M Tris-buffered saline (TBS, pH 8.2) containing 1% sodium deoxycholate (Sigma) (DOC) was mixed with 100,000 cpm (specific activity 125 uCi/ul) of $[^{125}I]$-TGF-B2 for 2 hr at room temperature. To this solution, 50 ul of a 50% suspension of goat anti-mouse IgG-agarose (Zymed) was added in TBS-DOC buffer for an additional 45 min with rocking. The agarose beads were washed 3× by centrifugation in TBS-DOC. The pelleted agarose was counted in a gamma counter (Beckman Gamma 5500, Palo Alto, Calif.). Addition of 1% DOC was necessary to limit nonspecific binding of the TGF-B to anti-Ig-agarose.

Figure 4:
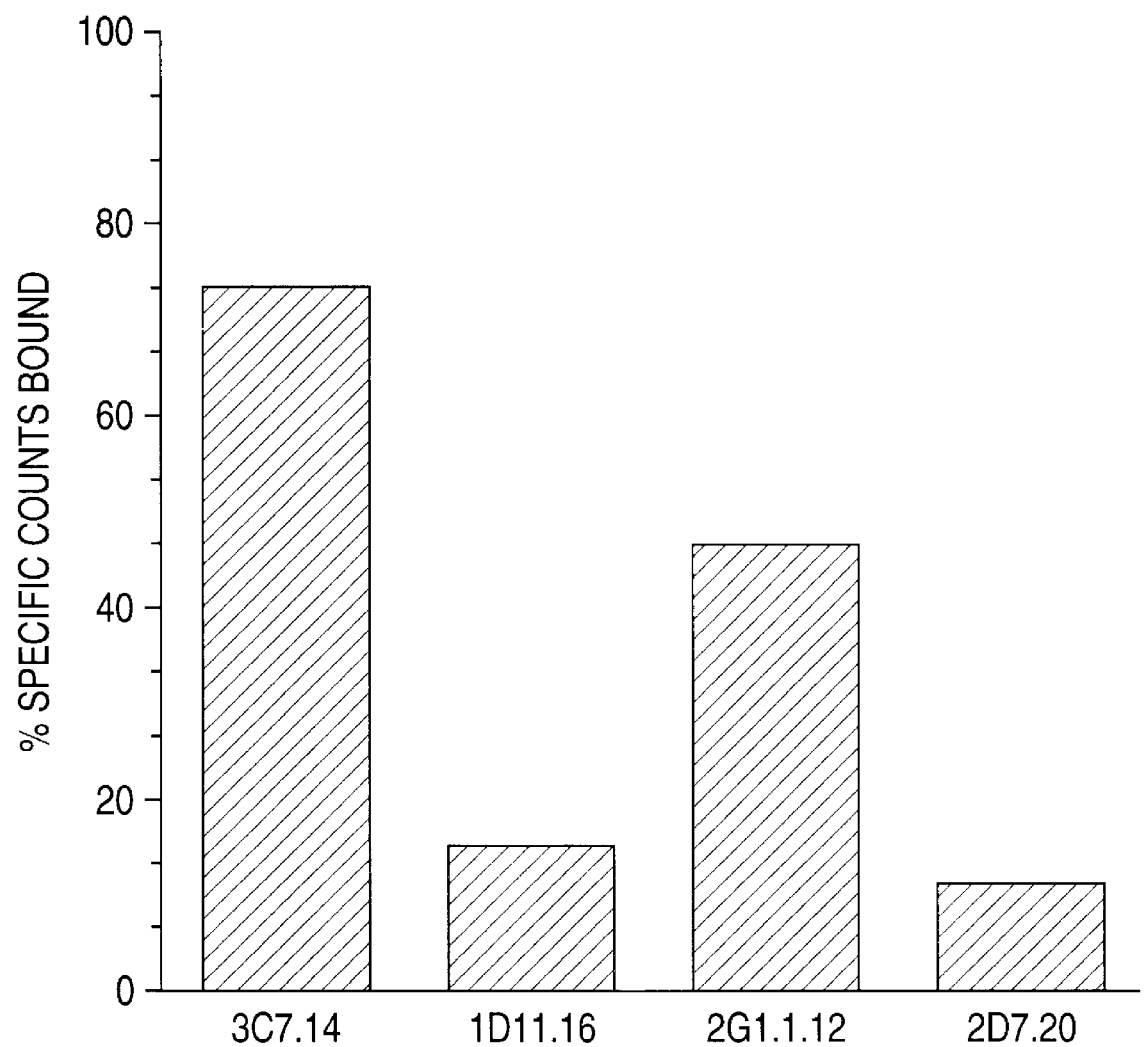
FIG. 4 illustrates the immunoprecipitation of [$^{125}$I]-labeled TGF-B2.

FIG. 4 shows that the immune complexes are brought down most effectively by the antibody 3C7.14. Counts are expressed as percent specific counts (CPM sample minus nonspecific background/total CPM minus non-specific background). A fair amount of batch to batch variation in the percentage of iodinated TGF-B2 brought down by all the MAbs was observed. This suggests that the chloramine T iodination procedure may convert a considerable amount of the TGF-B into an antigenically altered conformation.

EXAMPLE 8

(Antibody Purification)

The MAbs were purified either from culture supernatant or ascites by protein A-Sepharose chromatography (Goding, *J Immunol Meth* (1976) 42:17) (Pharmacia Fine Chemicals, Uppsala, Sweden). The binding of the gamma 1 subclass MAbs, 1D11.16 and 2G1.1.12, to protein A was enhanced by addition of a commercially prepared binding buffer (Bio-Rad, Richmond, Calif.). Antibodies were eluted from the protein A-Sepharose with 0.05M glycine-HCl plus 0.15M NaCl buffer (pH 2.3), dialyzed overnight versus PBS and stored at −20° C. The gamma 1 subclass antibodies purified from supernatants were concentrated and partially purified by ammonium sulfate precipitation (50% saturated) prior to protein A-chromatography.

EXAMPLE 9

(Competitive RIA)

This solid phase RIA follows the procedure of Mariani et al, *J Immunol Meth* (1984) 71:43. Briefly, wells of a 96 well microtiter plate (Microtest III, Becton Dickenson, Oxnard, Calif.) were coated with purified MAbs at 100 ug/well overnight in 0.01M carbonate coating buffer (pH 9.6). The wells were washed with PT and blocked with PT containing 1% (w/v) gelatin for 60 min. The plates were then washed with PT and incubated with 2 fold dilutions of a solution containing non-labeled TGF-B2 (starting at 20 ug/mL) in PT plus 1% gelatin. To each well was added a constant amount of [$^{125}$I]-TGF-B2 (100,000 cpm; specific activity 100–150 uCi/ug). After 2–5 hr at room temperature, the plate was thoroughly washed. Individual wells were cut from the plate and counted in a gamma counter. Calculation of affinity constants was performed using a nonlinear regression analysis program (Antoni and Mariani, *J Immunol Meth* (1985) 83:61). The affinity constants, provided in Table 1, ranged from $1.6 \times 10^7$ L/mol to $3.4 \times 10^8$ L/mol.

EXAMPLE 10

(Acute Liver Injury)

A hepatotoxin, D-galactosamine, causes reproducible mortality, liver fibrosis, and maximal TG-F-B gene expression approximately 48 hours after administration. A rat model utilizing this hepatotoxin is useful for evaluation of TGF-B antibody therapeutic effects on acute liver fibrosis.

Twenty Sprague-Dawley rats were administered 1.6 g/Kg D-galactosamine intraperitoneally. Ten of the rats also received 2 mg/Kg TGF-B antibody (1D11.16) 2 hours prior to hepatotoxin administration, and at 24, 48, and 72 hours post administration. Two rats from each test group were sacrificed at 48 hours to evaluate antibody efficacy at peak TGF-B gene expression.

Histological examination revealed that anti-TGF-B treated animals exhibited reduced liver pathology. Northern blot evaluation of tissues from specimens treated with TGF-B antibody showed significantly decreased levels of collagen mRNA, and almost normal levels of serum albumin, in contrast to non-treated controls.

Modifications of the above-described modes for carrying out the invention that are obvious to those of skill in the fields of hybridoma technology, immunology, and related fields, are intended to be within the scope of the following claims.

We claim:

1. A method for neutralizing the inhibitory effects of transforming growth factor beta (TGF-β), which method comprises administering a therapeutically effective amount of a monoclonal antibody that neutralizes transforming growth factor-β1 and transforming growth factor-β2.

2. The method of claim 1 wherein the monoclonal antibody is obtained from hybridoma 1D11.16 having ATCC Accession No. HB 9849.

3. The method of claim 1 wherein said monoclonal antibody having a binding affinity for transforming growth factor β1 and transforming growth factor-β2 of at least $10^7$ M$^{-1}$.

4. The method of claim 1 wherein said monoclonal antibody is a murine antibody.

5. The method of claim 1 wherein said monoclonal antibody is an antigen-binding fragment of a monoclonal antibody.

6. The method of claim 1 wherein said monoclonal antibody is a chimeric monoclonal antibody, said chimeric monoclonal antibody comprising an antigen binding portion and a remainder portion, said antigen binding portion obtained from a monoclonal antibody that neutralizes transforming growth factor-β1 and transforming growth factor-β2 and said remainder portion obtained from human antibodies.

7. The method of claim 6 wherein said chimeric monoclonal antibody comprises the antigen binding portion obtained from the monoclonal antibody obtained from hybridoma 1D11.16 having A.T.C.C. Accession No. HB9849.

* * * * *